United States Patent [19]

Cherukuri et al.

[11] Patent Number: 5,004,595
[45] Date of Patent: Apr. 2, 1991

[54] MULTIPLE ENCAPSULATED FLAVOR DELIVERY SYSTEM AND METHOD OF PREPARATION

[75] Inventors: Subraman R. Cherukuri, Towaco; Tommy L. Chau, Bridgewater; Krishna P. Raman, Randolph; Angel M. Orama, Stanhope, all of N.J.

[73] Assignee: Warner-Lambert Company, Morris Plains, N.J.

[21] Appl. No.: 503,331

[22] Filed: Mar. 30, 1990

Related U.S. Application Data

[63] Continuation-in-part of Ser. No. 452,660, Dec. 18, 1989, which is a continuation-in-part of Ser. No. 329,742, Mar. 28, 1989, Pat. No. 4,933,190, which is a continuation-in-part of Ser. No. 945,743, Dec. 23, 1986.

[51] Int. Cl.[5] .............................. A23G 3/30
[52] U.S. Cl. .......................... 424/48; 424/49; 424/401; 424/440; 426/3; 426/5; 426/660; 426/549; 426/804; 426/96
[58] Field of Search .......................... 426/3-6, 426/96, 660, 549, 804; 424/48, 49, 401, 440

[56] References Cited

U.S. PATENT DOCUMENTS

| | | |
|---|---|---|
| 4,448,789 | 5/1984 | Yang .................................. 426/3 |
| 4,452,821 | 6/1984 | Gergely ............................. 426/5 |
| 4,485,118 | 11/1984 | Carroll et al. ..................... 426/3 |
| 4,568,560 | 2/1986 | Schobel ............................. 426/5 |
| 4,590,075 | 5/1986 | Wei et al. .......................... 426/5 |
| 4,597,970 | 7/1986 | Sharma et al. .................... 426/5 |
| 4,722,845 | 2/1988 | Cherukuri et al. ................. 426/5 |
| 4,752,485 | 6/1988 | Sharma et al. .................... 426/5 |
| 4,775,537 | 10/1988 | Calabro et al. .................... 426/5 |
| 4,775,537 | 10/1988 | Calabro et al. .................... 426/3 |
| 4,800,091 | 1/1989 | Glass et al. ....................... 426/3 |
| 4,839,184 | 6/1989 | Cherukuri et al. ................. 426/5 |
| 4,911,934 | 3/1990 | Yang et al. ........................ 426/5 |
| 4,931,293 | 6/1990 | Cherukuri et al. ................. 426/5 |
| 4,933,190 | 6/1990 | Cherukuri et al. ................. 426/5 |

*Primary Examiner*—Jeanette Hunter
*Attorney, Agent, or Firm*—Daniel A. Scola, Jr.; Richard S. Bullitt

[57] ABSTRACT

A free-flowing particulate delivery system for providing enhanced flavor and sweetness to comestible compositions comprising a powdered flavor composition encapsulated in a matrix comprising an outer hydrophilic coating containing up to the solubility limit of the coating of an intense sweetener. The delivery system is particularly useful in chewing gums, confectioneries and pharmaceutical preparations as well as other food products.

22 Claims, 1 Drawing Sheet

MULTIPLE ENCAPSULATED FLAVOR DELIVERY SYSTEM AND METHOD OF PREPARATION

RELATED APPLICATIONS

The present application is a continuation-in-part of co-pending application Ser. No. 452,660, filed Dec. 18, 1989 by the inventors herein, which is in turn a continuation-in-part of co-pending application Ser. No. 329,742, filed Mar. 28, 1989, now U.S. Pat. No. 4,933,190 which is in turn a continuation-in-part of co-pending application Ser. No. 945,743, filed Dec. 23, 1986, both of the last mentioned in the names of Subraman Rao Cherukuri and Gul Mansukhani. Applicants claim the benefit of all prior applications under 35 U.S.C. 120.

BACKGROUND OF THE INVENTION

This invention relates to a new delivery system for flavors and to the process for its preparation, which has use in a variety of products including comestibles such as chewing gum compositions, confections, pharmaceuticals, food products such as beverages and some baked goods, dentifrice compositions and denture adhesives and in packaging applications. More particularly, this invention relates to a process for preparing a flavor delivery system which facilitates the delivery of higher levels and intensity of flavor without the harshness or off notes that is experienced at higher flavor concentrations.

Flavor delivery systems are well known in the art which may be divided into various classes based upon their physical states, namely, liquids, emulsions, pastes or solids. Not only are these states different but the potential uses for each state also differ as do their method of manufacture.

Over the years considerable effort has been directed toward the preparation of flavoring materials. Specifically, flavor materials have been sought that provide greater flavor intensity coupled with sustained flavor release for long periods of time.

An outgrowth of this activity has been the observation that when free flavor oil is added to gum base, only about 5% to 40% of the initial flavor oil is released from the gum upon chewing. It appears that as much as 80% of the remaining flavor oil becomes irreversibly bound to the gum base and cannot be chewed out.

To overcome this difficulty with flavor oils in particular, various attempts have been made to encapsulate the flavor oils or use dried ingredients to inhibit the gum base binding action. In addition, considerable effort has been directed to the development of delayed release flavoring agents that will delay release of the flavoring agent while permitting uniform release of the flavor over an extended period of time. The obvious benefit of immediate/delayed release is the ability to provide uniform flavor sensation during the entire consumption period which has not been previously attainable by the direct incorporation of conventional seasonings and flavor oils into chewing gum formulations.

Spray drying is one of the most widely used techniques for encapsulating or fixing a flavor. In this procedure a flavor oil is usually blended with a film forming agent dispersed in water and then emulsified to form a stable emulsion. Emulsification is necessary because flavor oils are insoluble in the water needed to dissolve the film forming agent. Obtaining an emulsion of low viscosity, at high solids content, is critical to producing an acceptable product. Stability at higher temperatures is also critical to avoid volatilization of the flavor oil. Maintaining low inlet temperatures (i.e. around 155° C.) as well as minimizing the residence time in the dryer are beneficial if the flavor is chemically unstable. The air drying conditions depend on the emulsion and product characteristics such as particle size of the product required. Modifications to the use of heat to remove the water from the emulsion have also been attempted. Some of these include the use of a dehydrating solvent as the drying medium rather than hot air. Freeze drying has also been contemplated.

Flavor fixation has also been obtained by the extrusion method wherein the flavor oil is coextruded with a water soluble sugar or sugar mixture, dried and ground for use. These products find application in dry mixes for instant release of the flavor on contact with water. Such products generally contain 10 to 15% by weight of flavor oil.

An extensive discussion of the prior art with respect to the extension of flavor is found in Wei et al U.S. Pat. No. 4,590,075. The patentees discuss the preparation of encapsulated flavors which are added together with a quantity of a non-confined hydrophobic flavor oil to a suspension agent before formulation in a chewing gum (Marmo et al. U.S. Pat. No. 3,920,849); the encapsulation of flavor in high molecular weight material such as polyvinyl acetate (Ogawa et al. U.S. Pat. No. 3,826,847); the preparation of a flavor composite by crosslinking the flavor with a water-insoluble hydrophilic polymer such as hydroxyethyl acrylate (U.S. Pat. No. 3,761,286); and the preparation of microencapsulated flavor particles and their dispersion in a slurry on the surface of a chewing gum (U.S. Pat. No. 3,962,463). Further, Yang et al. U.S. Pat. No. 4,695,463 is noted and discloses a flavor delivery system that relies on the immobilization of the flavor within a crosslinked hydrocolloid multivalent alginate or carageenate matrix.

Further, Sharma et al. U.S. Pat. No. 4,597,970 prepares a delivery system for actives such as sweeteners and including flavors which utilizes a hydrophobic matrix comprising edible fatty acids or waxes, lecithin and a glyceride component. This system is urged to provide a protective barrier and controlled release characteristics to the active so contained. The combination of materials in the encapsulating matrix provides wetting capabilities with respect to non-uniform core materials such as aspartame, while providing improved heat stability and thereby, extended high temperature processing capability. These attributes were frequently achieved at a cost of delay in release of the active.

Darragh et al. U.S. Pat. No. 3,867,556 also encapsulated volatile flavors in a fat or wax material. The patentees had found that the initial or base encapsulation displayed excessive instability to heat, and as their product was intended primarily for incorporation into baked goods, they applied a second coating of a water-soluble material such as gum arabic, which would provide high temperature stability while conferring rapid disintegration on contact with moisture. The Darragh et al. product likewise exhibited delayed flavor release.

Further, Merritt et al. U.S. Pat. Nos. 4,515,769 and 4,386,106 both to disclose the encapsulation of flavor material in a partially hydrophilic matrix comprising gelatin, a natural gum (or albumin as disclosed in the '769 Patent) or a plasticizer. This combined encapsulant was placed in an emulsion with the flavoring agent and thereafter dried to a solid matrix which was then ground to a base powder. The base powder was then coated with a water-insoluble material which purported to prevent flavor loss and delay flavor release in contact with moisture. Merritt et al. sought only to achieve a burst of flavor when the physical mastication of their flavor composite ruptured the outer encapsulating material. Merritt et al. may also be consulted in cumulative fashion for their review of the literature relevant to their invention.

Bakal et al. U.S. Pat. No. 4,087,557 relates to the incorporation of an artificial sweetener directly into the ester gum component of a chewing gum base, to achieve a delay and corresponding extension in sweetener release (column 2, lines 31–42). The patent contemplates the incorporation of certain flavors, specifically, food acids such as tartaric acid, succinic acid, etc. directly into the ester gum component, however, indicates that conventional flavors such as flavor oils are added separately after the gum base constituents including the artificial sweetener containing-ester gum have been mixed with each other and cooled. The flavor component is incorporated into chewing gums prepared in accordance with the patent in the conventional fashion, i.e., by direct incorporation of artificial flavor and/or by the incorporation of flavor coated with a hydrophilic material such as gum arabic (see Bakal et al., Example 6). Bakal et al. accordingly offers no solutions to the problems of flavor delivery and extension of concern to the art.

Other approaches to the preparation of flavor composites, particularly with flavor oils, are noted. Thus, Swisher U.S. Pat. No. 3,041,180 discloses a process for extruding a flavor oil with glycerine and corn syrup solids to form an encapsulated extruded flavor oil. The solid was dried and yielded a particulate solid. Miller et al. U.S. Pat. No. 4,610,890 discloses another process for preparing an extruded flavor oil with sugar, a starch hydrolysate and an emulsifier.

Yang U.S. Pat. Nos. 4,448,789 and 4,569,852 discloses a novel flavoring agent—hydrophilic polymer—by blending the flavor with the polymer and blending while heating to prepare a homogenous product. Once coupled and ground, the product can be used as a flavoring for chewing gum and confectionery products.

Giel U.S. Pat. No. 4,271,202 relates to a spray-drying process for forming solid flavoring material capable of including high percentages of flavoring oil per total particulate unit of weight. Because of the high oil content possible, such spray-dried products found wide use in a number of beverages and other foods. However, it was also found that spray-dried flavors prepared by this and similar known methods typically exhibit a relatively limited shelf life. In addition, the high temperatures necessarily involved during spray-drying processes have been found to impair the flavor and aroma of various heat-sensitive oil flavors, such as those in citrus fruit. Furthermore, solids formed by spray-drying commonly exhibit hygroscopic characteristics making them difficult to handle and store.

In addition to these techniques, Gergely U.S. Pat. No. 4,452,821 is directed to a confectionery product, especially a chewing gum, that purports to offer prolonged, extended delivery of flavoring aroma and/or active pharmaceutical ingredient. This is accomplished by providing the flavoring, aroma or active pharmaceutical ingredient in a solid solution or mixture within a wax containing functional groups, said wax forming a homogeneous mixture of solid solution. The wax does not contain any functional groups and is substantially immiscible with the flavoring, aroma or active pharmaceutical ingredient.

The approaches to flavor modification discussed above all fall short of providing a flavor delivery system which achieves the advantages of flavor intensity and fullness inherent in flavor oils in combination with improved release and extension characteristics. In most instances, where a modified flavor of this type is incorporated into a chewing gum composition, the gum base and, in particular, the elastomer component sequesters the flavor and thereby prevents its release during the chew. Moreover, the plasticizers and softeners conventionally employed in gum formulations tend to increase moisture pickup and corresponding flavor migration and loss, so that the flavor that might be available for release on chewing is further diminished in content and resulting extent of release and sensation.

It can accordingly be seen from the foregoing discussion that a broad variety of techniques, including the formation of spray-dried particles from the combination of flavor oils with hydrophilic film forming materials, have been tried, but have resulted in products of limited acceptability. If high levels of flavor oil are incorporated, the resulting particles yield an excessively harsh and bitter taste sensation, and off notes are experienced. Conversely, the reduction of the flavor intensity to avoid such bitterness, reduces the concentration of flavor in the particles so that an undesirably large quantity of particles must be added to a particular product to provide the desired flavor sensation. Finally, regardless of which of these approaches is followed, the longevity of the flavor sensation is undesirably limited.

In commonly assigned co-pending application Ser. No. 452,660, a sweetener delivery system is disclosed which employs a multiple coating system based upon an inner or core coating of the primary or first sweetener, and a second outer coating prepared from a solution of a hydrophilic polymer having a quantity of a sweetener dissolved therein. The core may be prepared from hydrophobic or hydrophilic materials, while the outer coating is primarily a hydrocolloid. The system in this instance was developed to offer protection and improved up front delivery to difficultly processible intense sweeteners such as aspartame, and provides the advantages of protection of the primary active coupled with improved up front and long term delivery performance.

The present invention seeks to adapt the attributes of the sweetener delivery system of application Ser. No. 452,660 to the instance of flavors, to respond to the need for the development of a flavor delivery system which improves flavor intensity, presentation, longevity and release in combination with greater stability and protection of the active.

SUMMARY OF THE INVENTION

A flavor delivery system is disclosed that offers a combination of improved properties including improved flavor intensity with reduced bitterness, together with improved flavor extension and release characteristics when incorporated into chewing gums and other products.

The delivery system in its final form is a particulate, free-flowing material, intended to provide enhanced flavor and sweetness to comestible compositions, said delivery system comprising:

(a) a core comprising a flavor in particulate form; and (b) an encapsulating matrix for said core, said matrix comprising an outer coating of a hydrophilic polymer containing an intense sweetener, the outer coating prepared from a solution of the hydrophilic polymer and the sweetener, with the sweetener being present in the polymer solution in an amount ranging from about 0.1% to about 50% by weight as based on said solution, and preferably from about 3% to about 15% as based on said solution, the outer coating present in an amount of from about 2% to about 100% by weight and preferably from about 15% to about 50% by weight of the core;

(c) wherein the encapsulating matrix protects the flavor in the core and permits higher concentrations of flavor to be included without imparting bitterness to the resulting flavor delivery system, and promotes consistent taste release.

The inventive delivery system contemplates a delivery system for virtually any flavor preparation and includes flavors and in particular flavor oils that are spray dried, and flavors that are prepared in particulate form with fat or wax outer coatings, and microcapsules that are prepared with flavor oils encapsulated with liquid gelatin. The exact composition of the core may vary.

In particular, the delivery system is directed to those flavors which are spray dried. The term "spray dried flavor" is meant to include the powdered product resulting from a natural or synthetic flavoring agent, e.g., an oil or essence, being adsorbed into a particulate carrier medium such as a starch, gum arabic, sugar, maltodextrin, corn syrup, polyol and the like. These spray dried materials may be formed by any conventional spray drying techniques as well as through extrusion, grinding or coacervation methods.

The hydrophilic outer coating may comprise a hydrocolloid. The hydrocolloid may be generally selected from the group consisting of gums, pectins, alginates, mucilages, film forming carbohydrates, and mixtures thereof.

The hydrophilic outer coating confers the combined advantages of up front release of the flavor and reduced flavor bitterness or off notes due to its protective action and the presence of the sweetener which is believed to reside in intimate association contact with the flavor-containing core in the final delivery system. Flavor intensity and delivery is increased as greater amounts of flavor may be encapsulated without the development of deleterious bitterness, and consistent taste release is also promoted. These increased amounts of flavor are protected from degradative influences such as moisture and interaction with other ingredients in the case of chewing gums, so that both up front and long term flavor delivery are improved.

A further characteristic and advantage of the present flavor delivery system is that the resulting particles exhibit bioadhesive properties that are believed to promote a desired prolongation of the release of both actives. Thus, the gum film formers are theorized to coat the mouth and to thereby act in a bioadhesive fashion.

The present delivery system finds utility in a variety of food and confectionery products as an additive thereto, and it offers a combined sensation of flavor and sweetness. The same protection is provided to both actives and thereby the longevity and intensity of both flavor and sweetness release that are experienced is enhanced.

The delivery system may be incorporated into a variety of confections including hard and soft candies, chewing gums and particularly, low calorie, low moisture formulations, as well as in pharmaceutical preparations, as a part of tablet coatings, and in such novel products as "scratch-and-sniff" and aroma packaging.

The flavor delivery system of the present invention may be used alone or in combination with conventional flavors, including liquid flavors, other spray dried flavors and the like, as well as with optional sweeteners, in various edible products.

In a further embodiment, the present invention includes a chewing gum comprising a gum base, the present flavor delivery system and optionally, sweeteners, fillers, and other additives. Both sugar containing and sugarless gums are contemplated, including gums with high gum baselow carbohydrate content.

Accordingly, it is a principal object of the present invention to provide a flavor delivery system that can deliver high concentrations of flavor oil without bitterness.

It is a further object of the present invention to provide a flavor delivery system as aforesaid which provides improved flavor intensity and longevity.

It is a further object of the present invention to provide a flavor delivery system as aforesaid which provides improved stability to the flavor in the core.

It is a still further object of the present invention to prepare a flavor delivery system having included therein an artificial sweetener for the improved delivery of both flavor and sweetness.

It is a still further object of the present invention to provide chewing gum compositions or other comestible products, pharmaceutical products or oral hygiene products, each having contained therein the flavor delivery system of the present invention.

Other objects and advantages will become apparent to those skilled in the art from a consideration of the ensuing description which proceeds with reference to the following illustrative drawings.

DETAILED DESCRIPTION

Accordingly, the present invention relates to a flavor delivery system which, in its final form, is a particulate free-flowing material that offers improved flavor intensity with reduced bitterness, as well as improved extension and release characteristics for the flavor. The delivery system comprises:

(a) a core comprising a flavor in particulate form; and (b) an encapsulating matrix for said core, said matrix comprising an outer coating of a hydrophilic polymer containing an intense sweetener, the outer coating prepared from a solution of the hydrophilic polymer and the sweetener, with the sweetener being present in the polymer solution in an amount ranging from about 0.1% to about 50% by weight as based on said solution, and preferably from about 3% to about 15% as based on said solution, the outer coating present in an amount from about 2% to about 100% by weight and preferably from about 15% to about 50% by weight of the core;

(c) wherein the encapsulating matrix protects the flavor in the core and permits higher concentrations of flavor to be included without imparting bitterness to the resulting flavor delivery system, and promotes consistent taste release.

As previously discussed, the core may be prepared in a variety of ways, and may include all flavors that are capable of being formulated into particulate form either directly or by means of incorporation into or with a solid carrier composition. The core may be prepared with a variety of known flavoring agents, which may be included in both hydrophobic and hydrophilic carrier or encapsulating materials. The flavor content of the core may vary, and may broadly range from about 5% to about 90% by weight of the core, and preferably from about 5% to about 30% by weight thereof.

Suitable flavors may include synthetic flavoring liquids, such as synthetic flavor oils and flavoring aromatics and/or oil; and/or liquids, oleo resins or extracts derived from plants, leaves, flowers, fruits, etc., and combinations of these. Preferably, the flavor component may be selected from spearmint oil, cinnamon oil, oil of wintergreen (methylsalicylate) and peppermint oil, clove oil, bay oil, anise oil, eucalyptus oil, thyme oil, cedar leaf oil, oil of nutmeg, allspice, oil of sage, mace, oil of bitter almonds and cassia oil. Also, various artificial, natural or synthetic fruit flavorings such as vanilla and citrus oils including lemon, orange, grape, lime and grapefruit and fruit essences including apple, pear, peach, grape, strawberry, raspberry, cherry, plum, pineapple, apricot and so forth, are contemplated.

In the instance where a hydrophilic encapsulating material is used, suitable materials include sugars and polyols as well as various hydrocolloids such as gums, pectins, alginates, mucilages, film forming carbohydrates, and mixtures. In the instance where the carrier or encapsulating material is hydrophobic, suitable hydrophobic materials include fats and waxes.

Suitable fats include fatty acids such as hydrogenated or partially hydrogenated oils, with representative materials comprising palm oil, palm kernel oil, soybean oil, cottonseed oil, peanut oil, rapeseed oil, rice bran oil, sunflower oil, safflower oil and mixtures thereof. Other materials also useful as fats may be selected from monoglycerides, diglycerides, triglycerides, polyglycerol esters, sorbitol esters, and mixtures thereof.

Suitable waxes include natural waxes, synthetic waxes and mixtures thereof, and, in particular, comprise material selected from the group consisting of paraffin wax, beeswax, carnauba wax, candelilla wax, lanolin wax, bayberry wax, sugar cane wax, petrolatum, carbowax, spermaceti wax, rice bran wax, microcrystalline wax, and mixtures thereof.

Naturally, the foregoing is illustrative and not restrictive of suitable materials for inclusion in the encapsulating medium of the core, and the invention is considered to extend to unnamed equivalent materials within its scope.

More particularly, a variety of composite cores may be prepared, such as a core disclosed in co-pending application Ser. No. 393,442, wherein a solution mixture of a flavor and a resin such as rosin, are subsequently encapsulated by spray congealing within an encapsulating matrix comprising a fat or wax. An alternative preparation comprises a microcapsule preparation as disclosed in Barr U.S. Pat. No. 4,597,959 to the disclosure of which is incorporated herein by reference.

Specifically, liquid flavor is formed into droplets which are then disposed in microcapsules which may be prepared from gelatin, and adhesive binders such as gum arabic, a gelatin crosslinking agent such as glutaraldehyde, and sodium silicate. The flavoring material may constitute 85-95% by weight of the microcapsule, with the encapsulating wall material comprising the remainder. Naturally, the foregoing core formulations are illustrative only and should not be considered as limiting of the invention.

In a particular embodiment, the core may be prepared with a variety of flavor compositions by spray drying alone or in conjunction with a solid carrier composition. Sugar and polyols are the most common solid carriers used for spray drying flavors, although a variety of other conventional materials are available. The particular powdered flavor composition is not critical to the invention in any manner. Generally, a spray dried flavor composition will have carrier present in amounts of about 50 to 95% by weight, with the remainder comprising flavor oils or essences. The core of the delivery system is the powdered flavor composition. In addition to the flavor composition, any number of additional ingredients may be added such as sweeteners, drugs, fillers, etc.

Surrounding the core is an encapsulating, hydrophilic matrix. The hydrophilic matrix comprises an outer coating of a hydrophilic polymer containing an intense sweetener, the outer coating prepared from a solution of the hydrophilic polymer and the sweetener, with the sweetener being present in the polymer solution in an amount ranging from about 0.1% to about 50% by weight as based on said solution, and preferably from about 3% to about 15% as based on said solution, the outer coating present in an amount of from about 2% to about 100% by weight and preferably from about 15% to about 50% by weight of the core.

Both the core and the encapsulating matrix of the present invention may be prepared with a hydrocolloid. Suitable hydrocolloids may be generally selected from the group consisting of gums, pectins, alginates, mucilages, film forming carbohydrates, and mixtures thereof. Specifically, the hydrocolloid may be material selected from the group consisting of gum arabic, tragacanth, karaya, ghatti, agar, alginates, carrageenans, fucellan, psyllium, and mixtures thereof. The hydrocolloid may also be selected from polyvinyl pyrrolidone, gelatin, dextran, xanthin, curdan, cellulose, methylcellulose, ethylcellulose, hydroxyethyl cellulose, hydroxypropyl cellulose, hydroxypropyl methylcellulose, carboxymethyl cellulose, low methoxy pectin, propylene glycol alginate, polydextrose, modified starch, maltodextrin, and mixtures thereof.

The sweetener may be selected from natural and synthetic intense sweeteners, and in a preferred embodiment may comprise at least one first solid natural or artificial high intensity sweetener selected from the group consisting of amino acid-based sweeteners, chloro derivatives of sucrose, dihydroflavinol, hydroxyguaiacol esters, L-aminodicarboxylic acid gem-diamines, L-aminodicarboxylic acid aminoalkenoic acid ester amides, dipeptide sweeteners, glycyrrhizin, saccharin and its salts, acesulfame salts, cyclamates, steviosides, talin, dihydrochalcone compounds and mixtures there of one of the same group of sweeteners useful as the sweetener herein.

It is one of the advantages of the present invention that the outer coating can provide improved protection for the active and at the same time greatly enhance up front flavor release by permitting higher concentrations of flavor to be included without the development of bitterness and harshness. This is believed to be attributable at least in part to the presence of the intense sweetener in the vicinity of the flavor-containing core. At the same time however, the encapsulating matrix is improved because it is more effective although it is applied and is present in an amount that is substantially reduced from the fat/wax coatings that are often in use as the outer coating for the core material.

According to a further embodiment of the invention, a process is included for preparing a flavor delivery system capable of providing greater up front flavor while modulating flavor release and providing greater protection for the flavor. The process comprises:

(a) forming a particulate core containing a flavor;

(b) coating the resulting particulate core with an encapsulating matrix by a fluidized bed-type process, said encapsulating matrix comprising an outer coating of a hydrophilic polymer containing an intense sweetener, said outer coating prepared from a solution of the hydrophilic polymer and said intense sweetener, with said intense sweetener being present in the polymer solution in an amount ranging from about 0.1% to about 50% by weight of said solution, the outer coating present in an amount of from about 2% to about 100% by weight of said core; and (c) recovering the final plural coated particles;

(d) wherein the encapsulating matrix protects the flavor in the core and permits higher concentrations of flavor to be included without imparting bitterness to the resulting flavor delivery system, and promotes consistent taste release.

The preparation of the present delivery system begins with the preparation of the core flavor particle. This may vary depending upon the core particle to be prepared. For example, the core may comprise a spray dried flavor such as one prepared with a carrier such as gum arabic or gelatin. The flavor core may also be prepared with fats and/or waxes in which event processing may include spray congealing.

The preparation of the present composite continues with the preparation of a solution of the encapsulating matrix by the formation of an aqueous solution mixture of the intense sweetener and the hydrophilic coating material. Accordingly, an aqueous solution of the hydrophilic coating material is prepared, for example, by placing the hydrophilic coating material in solution in deionized water. The sweetener is then added to the resulting solution to form the aqueous solution mixture. Throughout the preparation of the outer coating, the temperature may be maintained at about 50° to about 60° C.

Thereafter the particles comprising the core of the present delivery system are coated with the encapsulating matrix or outer coating. The application of the outer coating to the core particle may be accomplished by the same techniques disclosed in Cea et al. U.S. Pat. No. 4,384,004 to for materials of this type, and accordingly a variety of coating techniques including fluidized bed coating procedures are useful. The preferred coating procedure is the fluidized bed procedure wherein particles of the core material are suspended in an apparatus that creates a strong upward air current or stream in which the particles move. The stream passes through a zone of finely atomized coating material which causes the passing particles to be coated, after which the coated particles move from the upward stream and travel downward in a fluidized condition countercurrent to a flow of heated fluidized gas whereupon they are dried. The particles may reenter the upward stream for a further coating or may be withdrawn from the coating apparatus. This exemplary method and apparatus are known as the Wurster Process and are set forth in detail in the following U.S. Patents, the disclosures of which are incorporated herein by reference: U.S. Pat. No. 3,089,824; U.S. Pat. No. 3,117,027; U.S. Pat. No. 3,196,827; U.S. Pat. No. 3,241,520; and U.S. Pat. No. 3,253,944.

The application of the outer coating may be conducted at temperature levels that are reduced from those of most encapsulation processes and are accordingly less likely to damage the treated particles. In particular, the outer coating process may operate at inlet temperatures on the order of 100° to 125° F., so that relatively mild heating of the particles takes place during the coating process. Naturally, the temperature may vary and the selection of an optimum temperature resides within the skill of the art.

As described above, the outer coating is prepared for use by the formation of a liquid capable of being uniformly atomized. Thus, the water soluble hydrocolloid materials may be prepared as aqueous solutions. If desired, other ingredients such as plasticizers may be added to improve the properties of the final coating. Suitable plasticizers include the glyceryl ester of sebacic acid, diethyl phthalate, glyceryl triacetate, tributyl citrate, acetylated monoglyceride, citric acid ester of monodiglyceride, adipate ester, and others. The plasticizers may be added in known effective amounts within the scope of the invention.

The instant delivery system can be incorporated in a number of ingestible products such as confections and the like, as well as chewing gum compositions, pharmaceutical preparations and denture products.

The resultant product of this invention is in powder or granulated form. The particle size is not critical to the delivery system and can be adjusted to accommodate a particular desired release rate and mouthfeel, depending on the vehicle, e.g., chewing gum, confection or pharmaceutical in which it is incorporated. The product can be used as is for various applications, e.g., as a topping on baked goods or as an additive in a denture adhesive. The coating matrix is useful for a variety of core materials in addition to flavors, such as sweeteners, drugs and other particulate materials which require a coating for protection, controlled release or for taste-masking.

In another embodiment, the flavor particles can be directly admixed with the encapsulating matrix mixture and then spread into sheets, allowed to cool and then ground into suitable particle sizes for use in comestible products. This method has disadvantages, however, since grinding tends to disrupt the continuity of the coating around the flavor particles and may result in a loss of protection provided by the intimate contact between the encapsulating matrix and the flavor particle itself. Thus, while it is useful in practicing the instant invention, it is preferred to use a fluidized bed coating method as described above.

As previously mentioned, the hydrophilic coating provides both a protective barrier to prevent interaction between the flavor particles and other components or chemicals present in a particular product, as well as providing a means to increase the content of certain flavors which demonstrate bitterness at higher concentrations. While it is not critical that the hydrophilic coating be a particular thickness, it should be present to effectively coat the flavor particles. If additional coating is required the delivery system particles can be left suspended in the air stream and additional spraying with the solution of the outer coating can be performed.

The present flavor delivery system is useful in a number of comestible products. In particular, chewing gum, confectionery, pharmaceutical preparations, as well as other food products such as baked goods, are among those comestible products which would benefit through enhanced flavor/sweetness provided by the inventive delivery system.

With regard to the chewing gum formulation in which the novel delivery system is employed, the amount of gum base employed will vary greatly depending on various factors such as the type of base used, consistency desired and other components used to make the final product. In general, amounts of about 5% to about 45% by weight of the final chewing gum composition are acceptable for use in chewing gum compositions with preferred amounts of about 15% to about 25% by weight. The gum base may be any water-insoluble gum base well-known in the art. Illustrative examples of suitable polymers in gum bases include other natural and synthetic elastomers and rubbers. For example, those polymers which are suitable in gum bases include, without limitation, substances of vegetable origin such as chicle, jelutong, gutta percha and crown gum. Synthetic elastomers such as butadienestyrene copolymers, isobutylene-isoprene copolymers, polyethylene, polyisobutylene and polyvinylacetate and mixtures thereof are particularly useful.

The gum base composition may contain elastomer solvents to aid in softening the rubber component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include the pentaerythritol ester of partially hydrogenated wood rosin, pentaerythritol ester of wood rosin, glycerol ester of tall oil rosin, glycerol ester of wood rosin and partially hydrogenated wood rosin and partially hydrogenated methyl ester of rosin, such as polymers of alpha-pinene or beta-pinene; terpene resins including polyterpene and mixtures thereof. The solvent may be employed in an amount ranging from about 10% to about 75% and preferably about 45% to about 70% by weight of the gum base.

A variety of traditional ingredients such as plasticizers or softeners such as lanolin, stearic acid, sodium stearate, potassium stearate, glycerol triacetate, glycerine and the like are useful, as well as natural waxes and petroleum waxes, such as polyurethane waxes, paraffin waxes and microcrystalline waxes. These ingredients may also be incorporated into the gum base to obtain a variety of desirable textures and consistency properties. These additional materials are generally employed alone or in combination in amounts of up to about 30% by weight and preferably in amounts of from about 3% to about 20% by weight of the final gum base composition.

The chewing gum composition may additionally include the conventional additives such as sweeteners, coloring agents such as titanium dioxide; emulsifiers such as lecithin and glycerol monostearate; and additional fillers such as aluminum hydroxide, alumina, aluminum silicates, calcium carbonate, and talc and combinations thereof. These fillers may also be used in the gum base in various amounts. Preferably the amount of fillers when used will vary from about 4% to about 30% by weight of the final chewing gum.

In the instance where auxiliary flavors are utilized in addition to those in the delivery system, the present invention contemplates the inclusion of those flavors well-known in the art, including both natural and artificial flavors, and mints such as peppermint, menthol, artificial vanilla, cinnamon, various fruit flavors, both individual and mixed, and the like are contemplated. The flavorings are generally utilized in amounts that will vary depending upon the individual flavor, and may, for example, range in amounts of about 0.5% to about 3% by weight of the final chewing gum composition weight. The flavorings may be present in the delivery system, in the chewing gum composition itself, or both.

Suitable sweeteners that may be independently added include both natural and artificial sweeteners. Thus, sweeteners may be chosen from the following non-limiting list: sugars such as sucrose, glucose (corn syrup), dextrose, invert sugar, fructose and mixtures thereof; chlorinate sucrose compounds such as sucralose and its derivatives; acid saccharin and its various salts such as the sodium saccharin or calcium saccharin; cyclamic acid and its various salts such as the sodium salt; the dipeptide sweeteners such as aspartame and various derivatives known to be sweet; dihydrochalcone compounds; glycyrrhizin; Stevia rebaudiana (Stevioside); and sugar alcohols such as sorbitol, sorbitol syrup, mannitol, xylitol and the like. Also contemplated as sweeteners are the nonfermentable sugar substitute (hydrogenated starch hydrolysate) which is described in U.S. Reissue Pat. No. 26,959; and the synthetic sweetener 3,6-dihydro-6-methyl-1,1,2,3-oxathiazin-4-one-2,2-dioxide, particularly the potassium (Acesulfame-K), sodium and calcium salts thereof as described in German Patent No. 2,001,017.7.

The colorants useful in the present invention include the pigments such as titanium dioxide, and may be incorporated in amounts of up to about 1% by weight, and preferably up to about 0.6% by weight. Also, the colorants may include other dyes suitable for food, drug and cosmetic applications, and known as F.D.&C. dyes and the like. The materials acceptable for the foregoing spectrum of use are preferably water-soluble. Illustrative examples include indigoid dye, known as F.D.&C. Blue No. 2, which is the disodium salt of 5,5'-indigotindisulfonic acid. Similarly, the dye known as F.D.&C. Green No. 1 comprises a triphenylmethane dye and is the monosodium salt of 4-[4-N-ethyl-p-sulfobenzylamino)diphenylmethylene] amino)diphenylmethylene]-[1-(N-ethyl-N-p-sulfoniumbenzyl)-$^{2,5}$-cyclohexadienimine]. A full recitation of all F.D.&C. and D.&C. and other corresponding chemical structures may be found in the Kirk-Othmer Encyclopedia of Chemical Technology, in Volume 5, at pages 857–884, which text is accordingly incorporated herein by reference.

The chewing gums of the invention may be in any form known in the art, such as stick gum, slab gum, chunk gum, shredded gum, hard coated gum, tableted gum, as well as center-filled gum.

The present invention also includes a method for preparing a chewing gum composition having improved flavor intensity and sustained flavor release properties, which method broadly comprises:

(1) preparing the present flavor delivery system;

(2) adding the flavor delivery system prepared in Step 1 to a homogeneous mixture of a gum base and remaining chewing gum ingredients; and (3) forming the resultant mixture into suitable chewing gum shapes.

More particularly, the process of preparing a chewing gum composition in accordance with the invention is as follows. First, the gum base is melted (about 85° to about 90° C.), cooled to 78° C. and placed in a prewarmed (60° C.) standard mixing kettle equipped with sigma blades. An emulsifier (lecithin) is added and mixed. Next, a portion of the sugar alcohol (sorbitol) and the softener (glycerin) is added and mixed for an additional 3 to 6 minutes. The mixing kettle is cooled and additional sweetener (mannitol) and the remainder of the sorbitol and glycerin are then added and mixing is continued. At this time, the unflavored chewing gum temperature is about 39°–42° C. The flavor delivery system containing the core material is then added and incorporated into the base, and mixing is continued for an additional 1 to 10 minutes. The final gum temperature is 39°–43° C. The chewing gum composition is then discharged from the kettle, rolled, scored and formed into chewing gum pieces.

The following examples serve to provide further appreciation of the invention but are not meant in any way to restrict the effective scope thereof. All percentages throughout the specification are by weight % of the final delivery system unless otherwise indicated.

EXAMPLE 1

Delivery systems of the instant invention were prepared in accordance with the method described hereinabove. Specifically, a quantity of 500 grams of the core was prepared by conventional spray drying procedures, and comprised an encapsulation containing 20% by weight of peppermint flavor, with the remainder gum arabic as a carrier.

A quantity of 285.7 grams of the encapsulation matrix was prepared with an intense sweetener by the addition of gum arabic to deionized water to form a solution. The sweetener acesulfame-K was then added to the resulting solution to form the aqueous coating solution. The final coating solution contained 10% gum arabic, 20% acesulfame-K and 65% deionized water.

The encapsulation matrix was then applied to the core by a fluidized bed coating procedure. Accordingly, the coating was now ready to be fed into a spray congealing apparatus (Glatt GPCG-1) fluidized bed granulator where it would be used to coat a fluidized bed of the powdered spray-dried flavor. The flavor-particles were suspended in the granulator stream of cool air into which the coating was sprayed or atomized. Upon contact with the cooler air temperature and fluidized flavor particles, the molten coating solidified onto the flavor particles and passed out of the upward air stream. The nozzle pressure and temperature was regulated to control the final particle droplet size.

The result was a dry particle or agglomerate, referred to herein as the delivery system, having an approximate elliptical or spherical shape. The delivery system particles could then be sized for a particular application or allowed to remain in the granulator to obtain additional encapsulation coats. When dried, the resulting particles were determined to contain 7.27% acesulfame-K and 12.73% flavor, both by dried weight of the final delivery system.

EXAMPLE 2

A further alternative delivery system in accordance with the present invention was prepared in accordance with the general procedures outlined earlier. Specifically, a quantity of 500 grams of a core was prepared in this instance by spray congealing, and comprised an encapsulation containing 20% by weight of a peppermint flavor with the remainder being a fat/wax mixture with an emulsifier, all in accordance with prior application Ser. No. 393,442.

As with the previous example, a quantity of 285.7 grams of a gum arabic containing encapsulation matrix was prepared with the intense sweetener acesulfame-K in a mixture which comprised 65% deionized water, 15% gum arabic and 20% acesulfame-K. The encapsulation matrix was then applied to the core by a fluidized bed coating procedure, and the coating was fed into a spray congealing apparatus (Glatt GPCG-1) fluidized bed granulator. The flavor particles were suspended in the granulator and the molten coating was disposed over and solidified onto the flavor particles to form the resulting dry particle or agglomerate. When dried, the resulting particles were determined to contain 7.27% acesulfame-K and 12.73% flavor, both by dried weight of the final delivery system.

EXAMPLE 3

An additional alternative delivery system was prepared in this example by the preparation of a core comprising microencapsulated flavor beads prepared in accordance with U.S. Pat. No. 4,597,959. In this instance, the beads contained 85% flavor and the remainder a coating composition of gelatin.

The beads were then coated with a matrix prepared from gum arabic and acesulfame-K to a quantity of 500 grams. The matrix contained 65% deionized water, 15% gum arabic and 20% acesulfame-K. The encapsulating matrix was then applied to the core by the fluidized bed coating procedures discussed above, and when dried, the resulting particles were determined to contain 62.96% flavor and 14.81% acesulfame-K, as calculated by dry weight of the final delivery system.

EXAMPLE 4

Two peppermint flavored gum compositions were prepared in accordance with the present invention, and as discussed hereinabove with respect to the preparation of chewing gum compositions. The gum compositions each contained an equal amount of free liquid flavor, with Sample A containing encapsulated flavor prepared in accordance with Example 1 above, while control Sample B contained a quantity of spray dried flavor and free acesulfame-K. The formulations of each of the sample gum compositions are set forth in Table 1, below.

TABLE 1

| INGREDIENTS | SAMPLE A | SAMPLE B |
| --- | --- | --- |
| Gum Base | 26.000% | 26.000% |
| Carbohydrates | 59.872% | 61.015% |
| Softeners | 9.350% | 9.350% |
| Liquid Flavor | 0.850% | 0.850% |
| Spray Dried Flavor* | — | 2.500% |
| Acesulfame-K (Free) | — | 0.285% |

TABLE 1-continued

| INGREDIENTS | SAMPLE A | SAMPLE B |
| --- | --- | --- |
| Example 1 Encapsulation** | 3.928% | — |

*20% by weight of liquid flavor loading in spray dried flavor
**2850 ppm acesulfame-K, 5000 ppm liquid flavor loading
Batch Size: 2000 grams Both compositions were prepared to batch sizes of 2,000 grams and were then finally formed for consumption. The gum samples were then subjected to comparative taste testing, to evaluate the amount of harshness, if any, that was perceived by an expert panel. The results of the comparative tests are set forth in FIG. 1.

Figure 1:
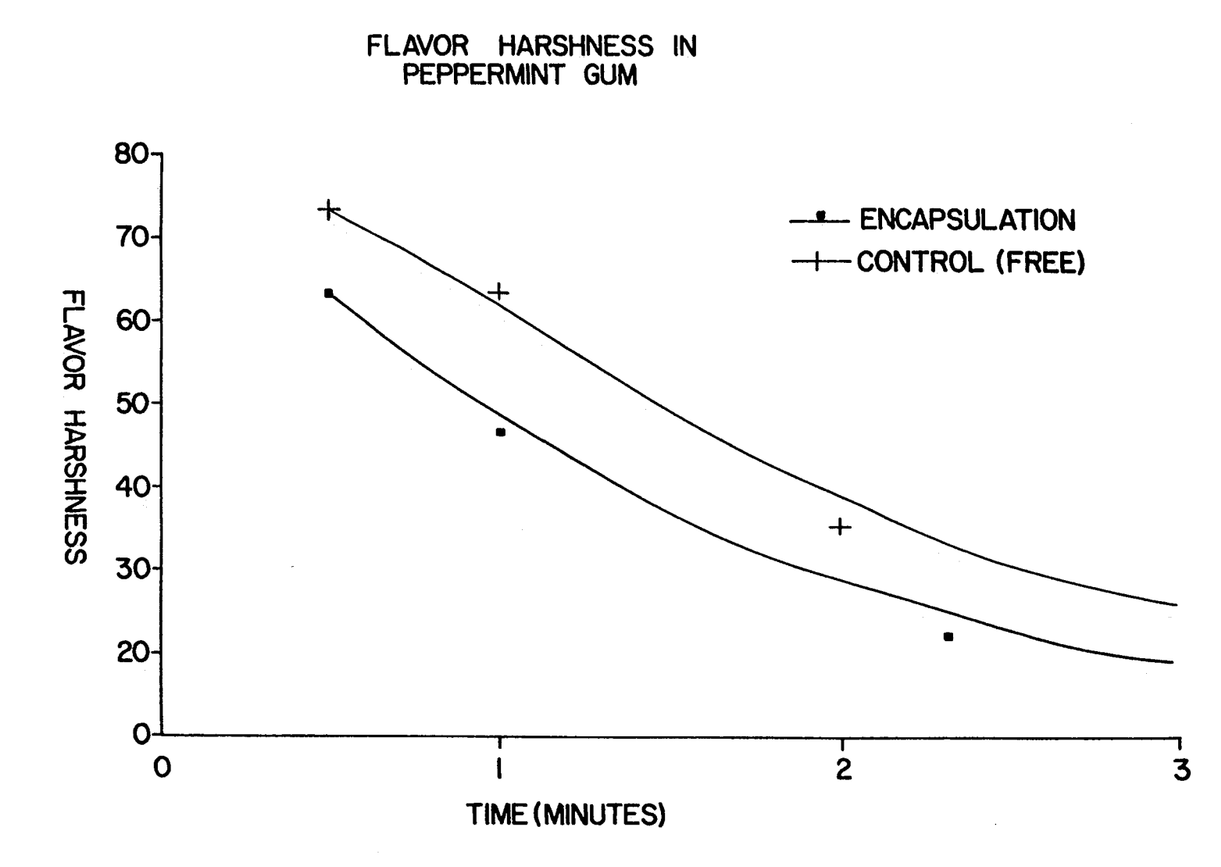
FIG. 1 is a graph comparing the flavor harshness in a peppermint flavored chewing gum prepared with the flavor delivery system of the present invention and a chewing gum prepared with conventional spray dried peppermint flavor as a control.

From a review of FIG. 1, the gum containing the encapsulated flavor of the present invention (Sample A) exhibited consistently lower harshness over time than the control gum composition utilizing the free acesulfame-K and the uncoated spray dried peppermint flavor. As indicated earlier, both compositions were prepared to contain the same quantity of flavor and acesulfame-K sweetener and, as such, clearly demonstrate the capability of the present flavor delivery system to reduce harshness. This reduction in harshness carries with it an ability to include greater quantities of flavor and to thereby improve the flavor experienced during the chew.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A free-flowing particulate delivery system for providing enhanced flavor and sweetness to comestible compositions, said delivery system comprising:
   (a) a core comprising a flavor in particulate form; and
   (b) an encapsulating matrix for said core, said matrix comprising an outer coating of a hydrophilic polymer containing an intense sweetener, said outer coating prepared from a solution of the hydrophilic polymer and said intense sweetener, with said intense sweetener being present in the polymer solution in an amount ranging from about 0.1% to about 50% by weight of said solution, the outer coating present in an amount of from about 2% to about 100% by weight of said core;
   (c) wherein the encapsulating matrix protects the flavor in the core and permits higher concentrations of flavor to be included without imparting bitterness to the resulting flavor delivery system, and promotes consistent taste release.

2. The delivery system of claim 1 wherein the core is a spray dried natural or artificial flavor or essence.

3. The delivery system of claim 2 wherein the spray dried flavor is selected from the group consisting of spearmint flavor, peppermint flavor, cinnamon flavor, fruit flavors, fruit essences, kola flavor, kola extract and mixtures thereof.

4. The delivery stem of claim 1 wherein the flavor composition is present in amounts of about 5 to about 90% by weight of the core.

5. The delivery system of claim 1 wherein the flavor composition is present in amounts of about 20 to about 30% by weight of the core.

6. The delivery system of claim 1 wherein the outer coating is selected from the group consisting of hydrocolloids, polysaccharides, polyols, and mixtures thereof.

7. The delivery system of claim 6 wherein said outer coating is selected from the group consisting of gums, pectins, alginates, mucilages, film forming carbohydrates, and mixtures thereof.

8. The delivery system of claim 6 wherein said outer coating is selected from the group consisting of gum arabic, tragacanth, karaya, ghatti, agar, alginates, carrageenans, fucellan, psyllium, and mixtures thereof.

9. The delivery system of claim 6 wherein said outer coating is selected from the group consisting of polyvinyl pyrrolidone, gelatin, dextran, xanthin, curdan, cellulose, methylcellulose, ethylcellulose, hydroxyethyl cellulose, hydroxypropyl cellulose, hydroxypropyl methylcellulose, carboxymethyl cellulose, low methoxy pectin, propylene glycol alginate, and mixtures thereof.

10. The delivery system of claim 1 wherein said outer coating is present in an amount of from about 15% to about 50% by weight of said core.

11. The delivery system of claim 1 wherein said sweetener is present in an amount ranging from about 3% by weight to about 15% by weight of the outer coating.

12. A process of preparing a flavor delivery system capable of providing greater up front flavor while modulating flavor release and providing greater protection for the flavor comprising:
   (a) forming a particulate core containing a flavor;
   (b) coating the resulting particulate core with an encapsulating matrix by a fluidized bed-type process, said encapsulating matrix comprising an outer coating of a hydrophilic polymer containing an intense sweetener, said outer coating prepared from a solution of the hydrophilic polymer and said intense sweetener, with said intense sweetener being present in the polymer solution in an amount ranging from about 0.1% to about 50% by weight of said solution, the outer coating present in an amount of from about 2% to about 100% by weight of said core; and
   (c) recovering the final plural coated particles;
   (d) wherein the encapsulating matrix protects the flavor in the core and permits higher concentrations of flavor to be included without imparting bitterness to the resulting flavor delivery system, and promotes consistent taste release.

13. A method of preparing a chewing gum composition having improved flavor intensity and sustained flavor release properties which comprises:
   (1) preparing a flavor delivery system by the method of claim 12;
   (2) adding the flavor delivery system prepared in step 1 to a homogeneous mixture of a gum base and remaining chewing gum ingredients; and
   (3) forming the resultant mixture into suitable chewing gum shapes.

14. The delivery system of claim 1 incorporated into a chewing gum composition.

15. The delivery system of claim 1 incorporated into a confectionery composition.

16. The delivery system of claim 1 incorporated into a pharmaceutical composition.

17. The delivery system of claim 1 incorporated into a food product.

18. The delivery system of claim 1 incorporated into a dentifrice composition or denture adhesive.

19. A hard confection including the delivery system of claim 1.

20. An oral hygiene preparation including the delivery system of claim 1.

21. An oral pharmaceutical preparation including the delivery system of claim 1.

22. A bakery product including the sweetener delivery system of claim 1.

* * * * *